United States Patent [19]

Akiyama

[11] Patent Number: 5,120,123
[45] Date of Patent: Jun. 9, 1992

[54] OPHTHALMIC MEASURING METHOD AND APPARATUS

[75] Inventor: Koichi Akiyama, Tsukuba, Japan
[73] Assignee: Kowa Company Ltd., Japan
[21] Appl. No.: 427,039
[22] Filed: Oct. 25, 1989
[30] Foreign Application Priority Data
 Oct. 28, 1988 [JP] Japan .................... 63-270699
[51] Int. Cl.$^5$ .................... A61B 3/10; A61B 300
[52] U.S. Cl. .................... 351/221; 351/205; 128/745
[58] Field of Search .............. 351/221, 205, 206, 208, 351/210, 211, 214; 128/745, 633; 606/4
[56] References Cited

U.S. PATENT DOCUMENTS 4,832,043  5/1989  Ichihashi .................... 128/745
4,854,692  8/1989  Kobayashi .................... 351/221
4,900,144  2/1990  Kobayashi .................... 351/206

Primary Examiner—Rodney B. Bovernick
Attorney, Agent, or Firm—Bruce L. Adams; Van C. Wilks

[57] ABSTRACT

Disclosed is an ophthalmic measuring method and aparatus in which an optical system is used to project a laser beam at a selected spot in camera oculi of the patient's eye to be examined, and the laser light scattered therefrom is detected for ophthalmic measurement. The light scattered from the selected spot is received by a photoelectric converter in at least two directions to derive signals representing the intensity of the scattered light in these directions. These signals are then compared to remove noise components, thereby providing an improvement in a S/N ratio.

11 Claims, 5 Drawing Sheets

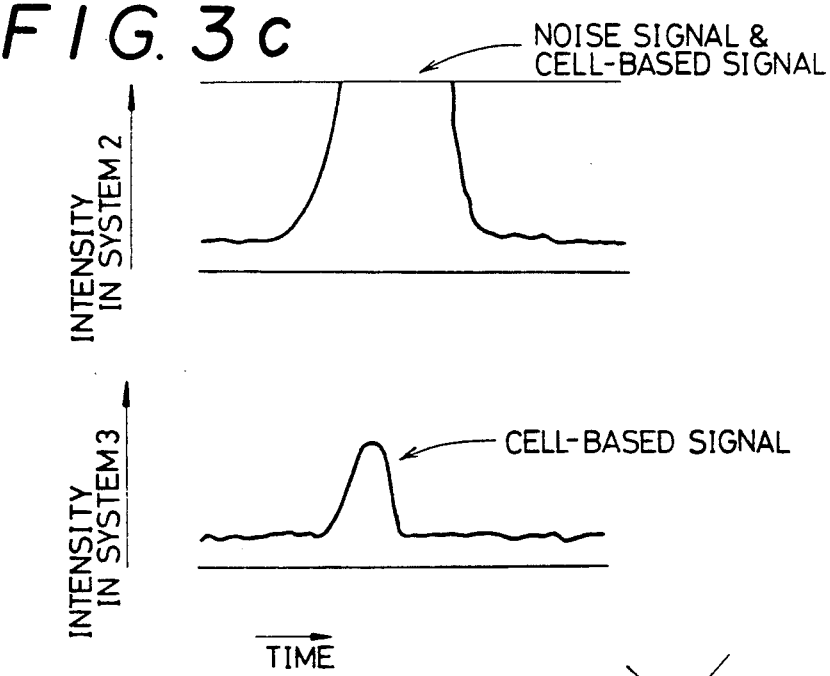
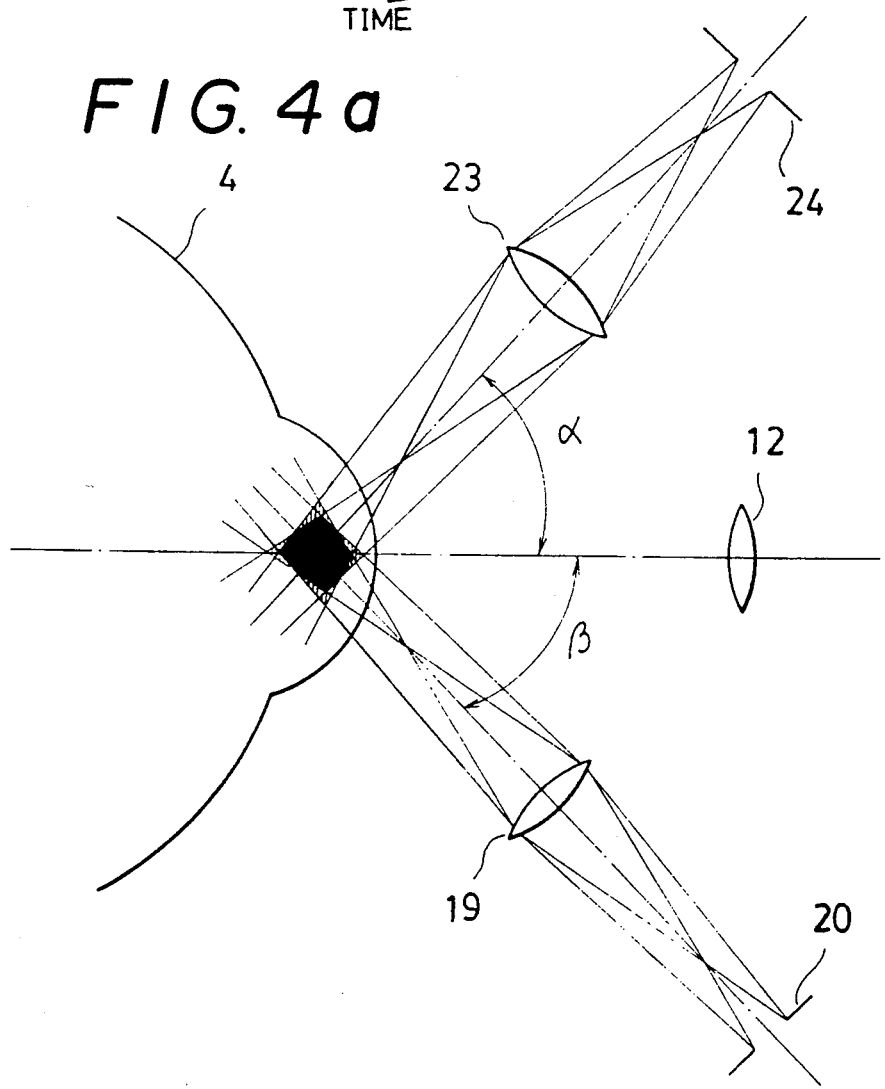

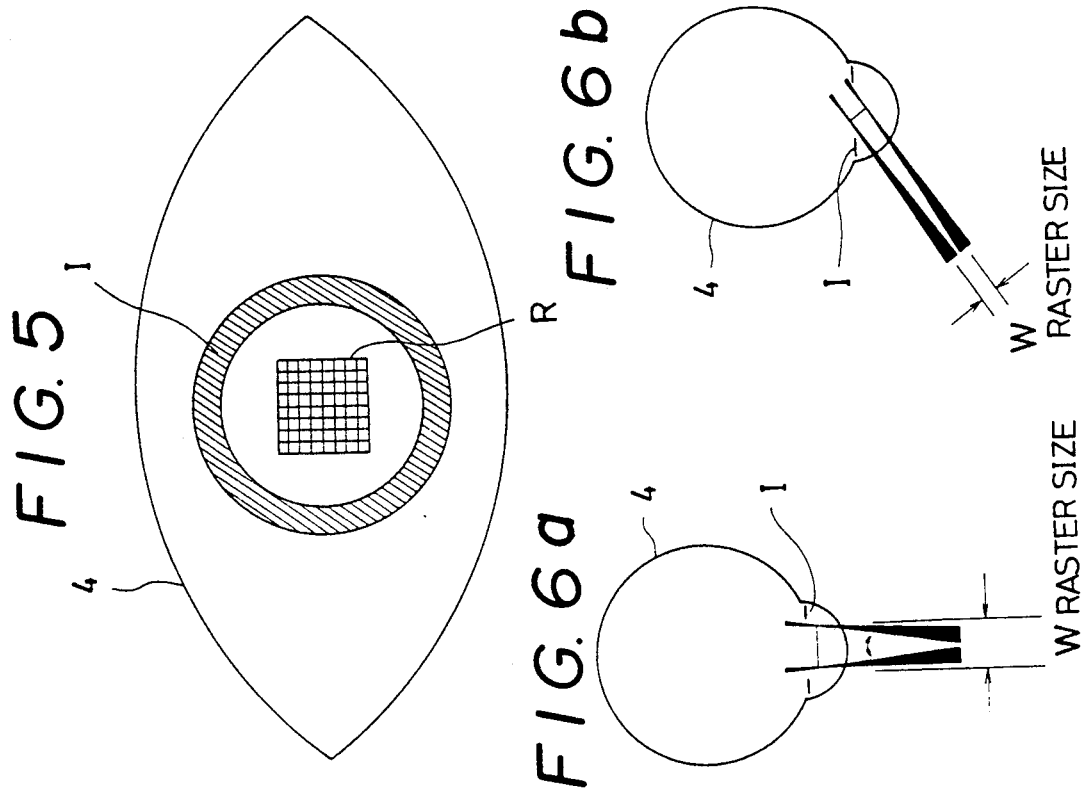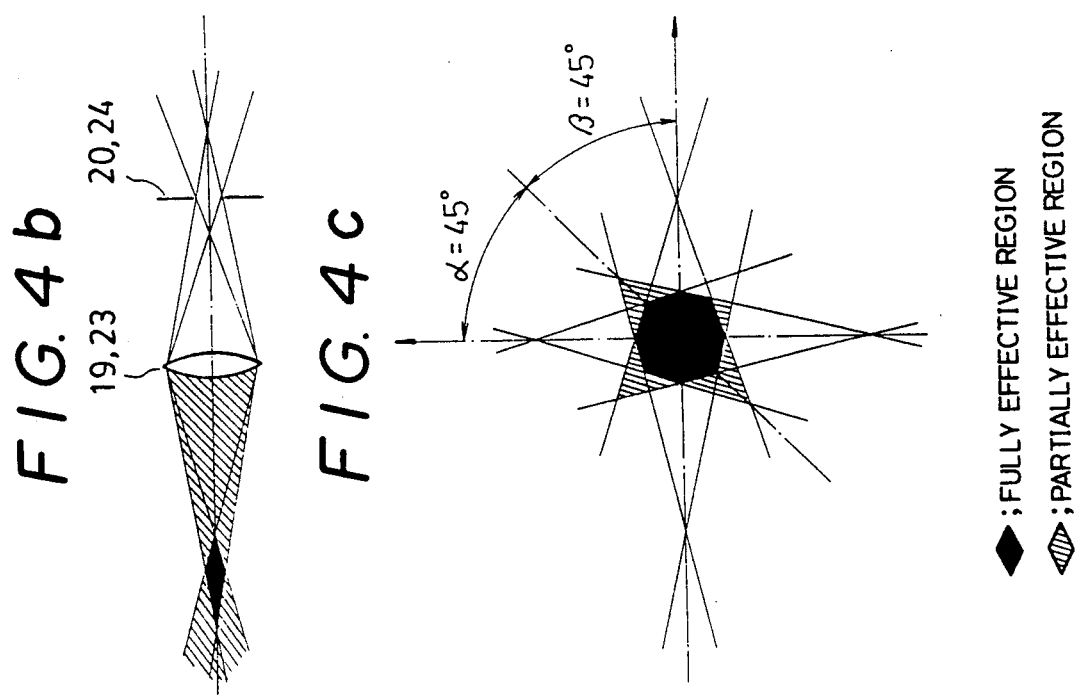

OPHTHALMIC MEASURING METHOD AND APPARATUS

BACKGROUND OF THE INVENTION

1. Field of the Invention

This invention relates to an ophthalmic measuring method and apparatus, and more particularly to an ophthalmic measuring method and apparatus in which an optical system is used to project a laser beam at a selected spot in the camera oculi of a patient's eye, particularly in the anterior chamber thereof, and the laser light scattered therefrom is detected.

2. Description of the Prior Art

Measurement of floating cells in the anterior chamber is very important in the diagnosis of ophthalmic inflammation and uveitis. Conventionally a slit lamp microscope is often used for this, with grading being via the naked eye, while on the other hand a photographic measuring method has been developed to provide quantitative measurements. However, no method has yet been perfected that is readily applicable to clinical examinations.

With the conventional method of naked-eye measurement in which judgment can vary depending on the person making the measurement, the data thus gained lacks reliability. One solution has been a method of ophthalmic measurement in which laser light is projected into the eye and the light scattering from the eye is detected and analyzed quantitatively (see, for example, U.S. Pat. No. 4,711,542).

When measuring scattered laser light, light reflecting and scattering from the cornea, the iris, the crystalline lens, including artificial crystalline lenses employed following a white cataract operation, shows up as noise in the scattered laser light and in the measurement site in the anterior chamber, which degrades measurement accuracy, prevents measured values from being reproduced and can cancel out the signal components.

To overcome these drawbacks, U.S. Pat. No. 4,832,043 discloses an ophthalmic disease detection apparatus in which a laser beam is deflected so far as to exceed the slit width formed on a mask in front of a photoelectric converter. In this apparatus, an electric signal derived from the photoelectric converter when the laser beam is deflected outside the slit width is subtracted from an electric signal obtained when the laser beam is deflected within the slit width, thereby removing noise components based on the dark current in the photoelectric converter or unnecessary scattered light or reflected light. Such a method to remove the noise is insufficient because the light scattered or reflected from the cornea or crystalline lens, which behaves itself as noise, has strong directivity so that it can directly impinge on the mask, thereby reducing a S/N ratio.

SUMMARY OF THE INVENTION

The object of the present invention is therefore to provide an ophthalmic measuring method and apparatus which enable the noise from reflected or scattered light which may impinge on the spot to be measured in the patient's eye to be reduced, thereby improving the accuracy of the measurement.

In accordance with the present invention, an ophthalmic measuring method and apparatus is provided in which an optical system is used to project a laser beam at a selected spot in the patient's eye, and the laser light scattered therefrom is detected for ophthalmic measurement. The light scattered from the selected spot is received in at least first and second different directions by a photoelectric converter to produce signals representing the intensity of the scattered light in these directions. The first and second directions are arranged to be symmetrical with respect to the direction along which the laser beam is projected. The signals in the first and second directions are then compared to remove noise components derived from the light reflected at a portion of the eye other than said selected spot in the eye.

With the above arrangement, the light scattered from the interior of the eye will indeed be oriented, but shows no strong directivity with respect to the angle of incidence, so that this light can simultaneously enter the two light-receiving means from the two different directions. However, owing to the strongly directional nature of the noise component in light reflected by the cornea or artificial crystalline lens, such light containing the noise component will only be able to enter one of the light-receiving means. Therefore, by comparing the signal intensities of the light received from the plurality of directions, it becomes possible to detect only the scattered light that is being used for the measurement in the camera oculi of the patient's eye without any noise component due to the directional light scattered or reflected at a portion other than the spot to be examined.

BRIEF DESCRIPTION OF THE DRAWINGS

The purposes and features of the present invention will become more apparent from a consideration of the following detailed description taken in conjunction with the accompanying drawings in which:

FIG. 2 is an explanatory drawing showing a side view of the apparatus shown in FIG. 1a;

FIGS. 3b and 3c are graphs each showing the output of the two light-receiving systems and explaining the effect of this invention;

FIG. 4a to 4c are explanatory drawings showing the effect of masks disposed in the light-receiving system;

FIG. 5 is an explanatory drawing showing the image observed by the person conducting the examination; and FIGS. 6a and 6b are drawings illustrating the advantages of front-face scanning.

DETAILED DESCRIPTION OF THE PREFERRED EMBODIMENTS

Figure 1A:
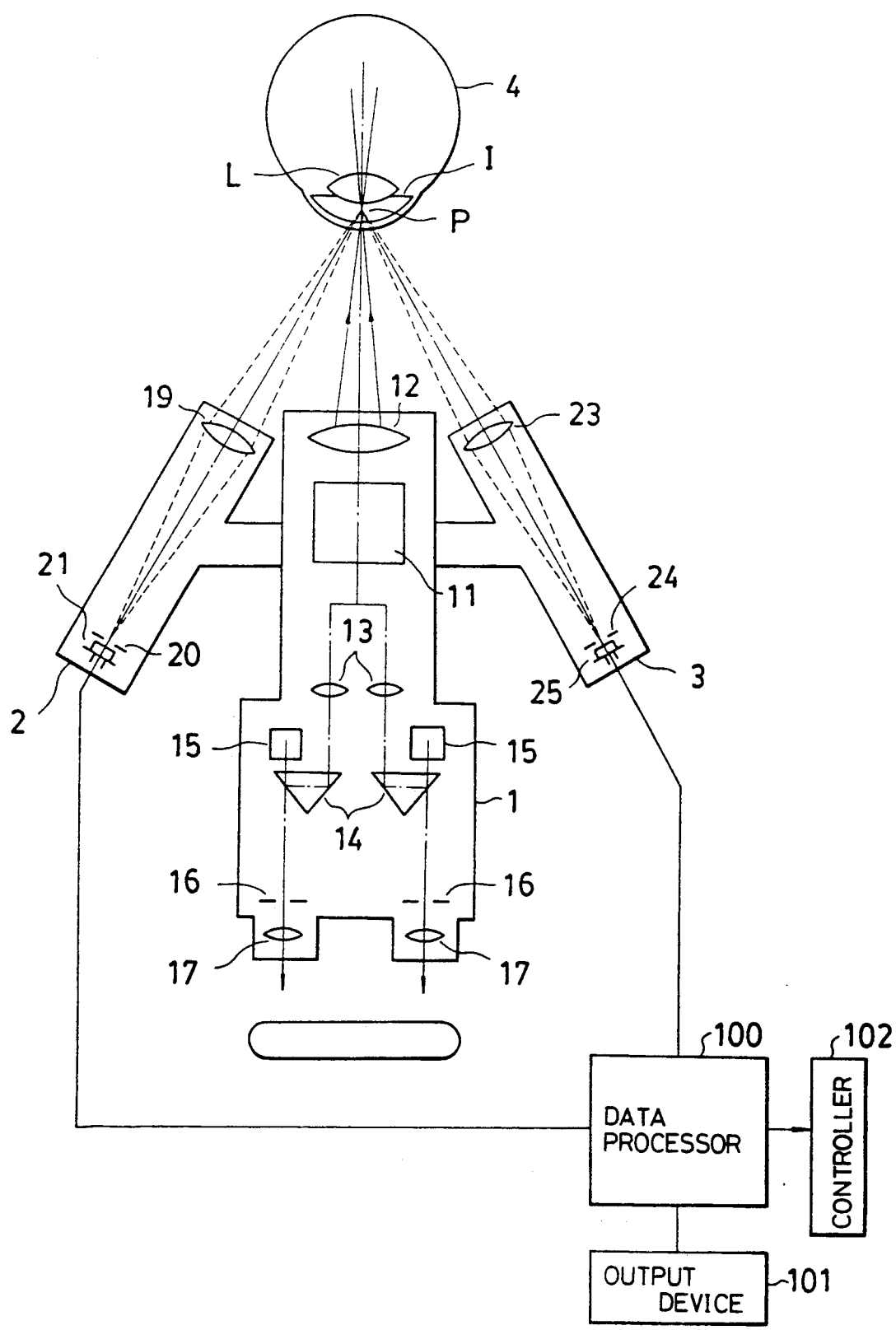
FIG. 1a is an explanatory drawing illustrating the construction of an ophthalmic measuring apparatus according to the present invention.

This invention is described in detail below on the basis of the preferred embodiments illustrated in the drawings.

Figure 2:
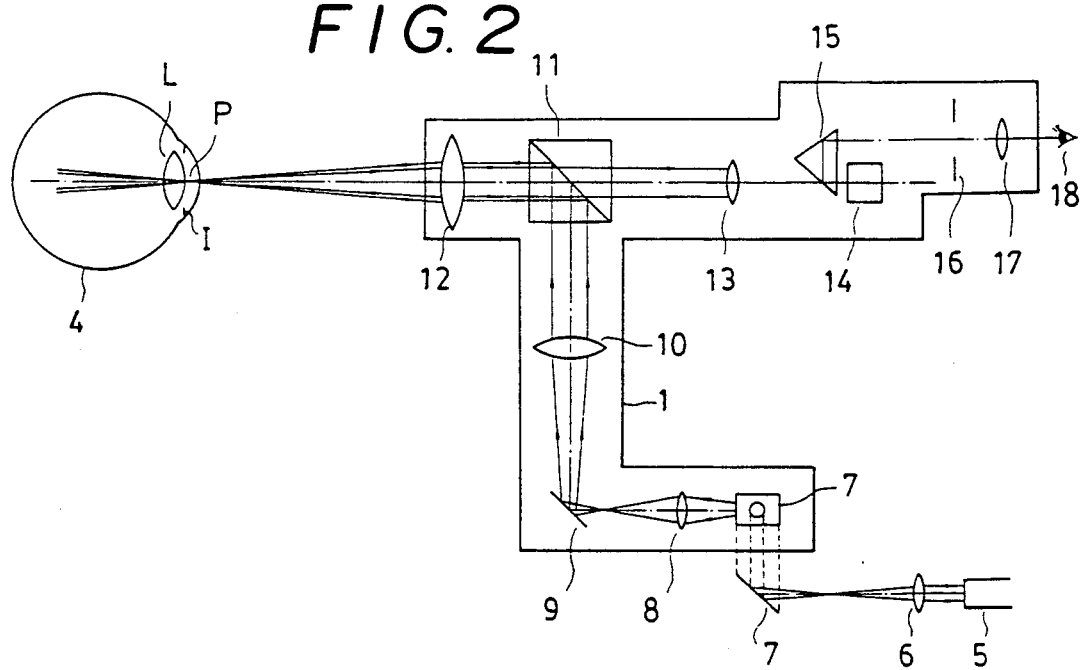

FIG. 1a is a plan view, and FIG. 2 a side view, of the construction of the optical system in the ophthalmic measuring apparatus according to the present invention.

With reference to FIG. 1a, a light projection and observation section 1 is provided with an optical observation system comprised of a condenser lens 12, a pair of lenses 13, a pair of prisms 14, a pair of prisms 15, and a pair of field stops 16. As shown in FIG. 2, the lower part of the optical observation system is linked to a light projection system via a beam splitter 11.

The light projection system is configured as follows. A beam of laser light from a laser light source 5 passes through a lens 6, an optical scanner 7 (such as a galvanometer mirror, for example), a lens 8, an optical scanner 9 (such as a galvanometer mirror, for example), a lens 10, the beam splitter 11 and a condenser lens 12 to converge in the anterior part of the eye being examined at a point of convergence P in front of the crystalline lens L and iris I.

The light projection system is arranged so that the point of convergence P is deflected vertically and horizontally ( two-dimensionally ) for raster-scanning by means of the optical scanners 7 and 9. This is described below in detail, with reference to FIG. 5.

As the laser beam is deflected, the impingement of the beam on a floating cell in the anterior chamber produces a pulse of scattered light. To evaluate this scattered light, optical receiving systems 2 and 3 are disposed symmetrically at each side of the light projection and observation section 1. Photoelectric converters 21 and 25 of the optical receiving systems 2 and 3 respectively, are located at positions that are each a conjugate of the point of convergence P, relative to lenses 19 and 23. Disposed in front of the photoelectric converters 21 and 25 are masks 20 and 24 respectively for regulating the size of the detection region. The effect of such an arrangement configuration is that light scattered by floating cells in the anterior chamber of the eye 4 under examination impinges virtually simultaneously on each of the photoelectric converters 21 and 25.

The outputs of the photoelectric converters 21 and 25 are fed, via an A/D converter means or the like (not shown), into a data processor 100 consisting of a microprocessor, memory and so forth. The outputs of the photoelectric converters 21 and 25 are evaluated by the data processor 100, as described later, and the result is output to an output device 101 (which is, for example, a printer, or CRT or liquid crystal display) as the result of the measurement of floating cells in the anterior chamber. The data processor 100 also drives the optical scanner 7 via a projected light control section comprised by controller 102 to control the laser-beam scanning of the eye 4 under examination.

The light projection and observation section 1 is positioned in front of the patient by a known alignment means. During this alignment the examiner uses a pair of eyepieces 17 to observe the region R being scanned in two dimensions by the laser beam passing through the center of the iris of the eye 4 under examination, as illustrated by FIG. 5. The light projection system is positioned in front of the eye 4 under examination so that the laser beam does not impinge on the iris I and can thus be deflected to maximize the range of the raster-scanning. That is, the size W of the scanned region, as limited by the iris I, is considerably larger when the raster scanning is performed from directly in front of the eye, as shown in FIG. 6a, compared to when the scanning is performed from off to one side, as in FIG. 6b. Other merits of frontal scanning are that movement by the patient is less likely to cause the laser beam to impinge on the iris, observation clearly is facilitated when the observation section is in front of the eye, and alignment is also easier.

The operation of the above configuration will now be described, starting with the basic measurement method using the above-described apparatus.

The apparatus shown in FIG. 1a and FIG. 2 is arranged so that scattered light from the convergence point P of the laser beam in the anterior chamber of the eye 4 under examination is detected from two different directions.

Figure 1B:
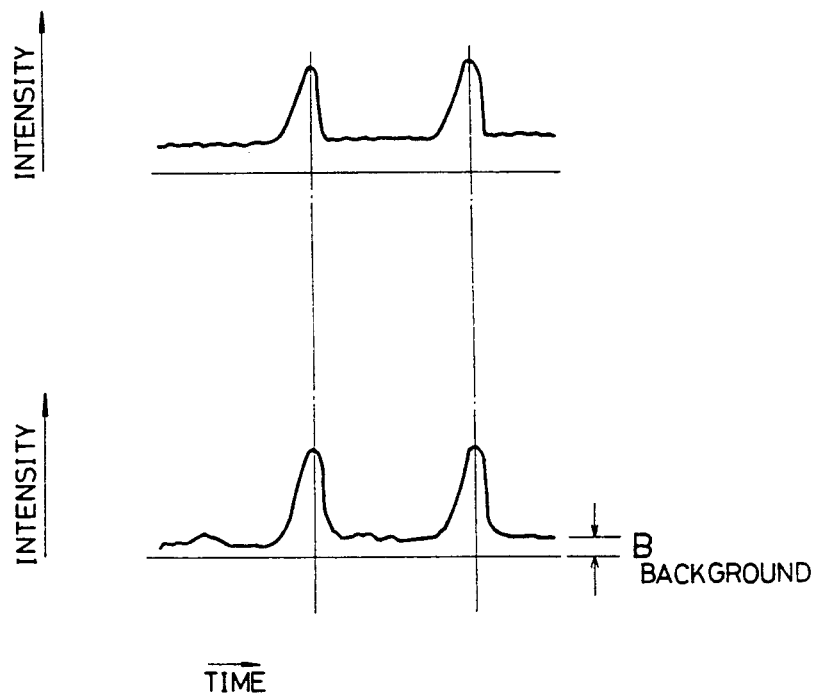
FIG. 1b is a graph showing the output of the two light-receiving systems.

In the measurement process, because the laser beam is raster-scanned, the intensity component of the light scattered by floating cells in the anterior chamber appears in the form of pulses, as shown by FIG. 1b, producing signals that stand out from the background intensity component B. Therefore, the data processor 100 only judges pulsed signals that are detected virtually simultaneously by the two optical receiving systems 2 and 3 as being signals produced by floating cells in the anterior chamber of the eye 4. These signals are counted to show the number of such cells and the count integrated is output to the output section 101, as is disclosed in U.S. Pat. No. 4,832,043 or No. 4,838,683).

With respect to the evaluation of the above light-receiving system output, the light returning to the light-receiving system will also, in addition to the scattered light component, include light reflected by the cornea and noise components generated in the course of the scanning. Especially when measuring floating cells in the anterior chamber, the measurement will be oriented by probability if the measurement volume becomes too small. To reduce a decrease in reproducibility of data, a certain amount of measurement volume is required. The method to count cells by the laser beam scattering, on the other hand, necessitates that the laser beam be converged to obtain a given level of scattered light intensity. Owing to the highly directional nature of laser light, the result is that directional reflected light is produced by reflection from the front and rear surfaces of the cornea and of the crystalline lens L. In addition, the extensive scanning range would eventually cause this reflected light to enter the light-receiving section. Such directional light reflected can be prevented from simultaneously entering both of the light-receiving means, if the light is received from two different directions, which are disposed to be symmetrical with respect to the direction along which the laser beam is projected. The light scattered from the floating cells to be measured, on the other hand, will be oriented, but not so directionally and can simultaneously enter the two light-receiving systems even from the two different directions.

This will now be explained with reference to FIGS. 3a to 3c. The laser beam which has passed through the condenser lens 12 and converged at the point of convergence P is raster-scanned in two dimensions by the optical scanners 7 and 9. Although measurement can be carried out using scanning in just one dimension, two-dimensional scanning is preferable because the measurement volume becomes larger. The following explanation is given only with reference to horizontal scanning, but applies equally well to vertical scanning.

Figure 3A:
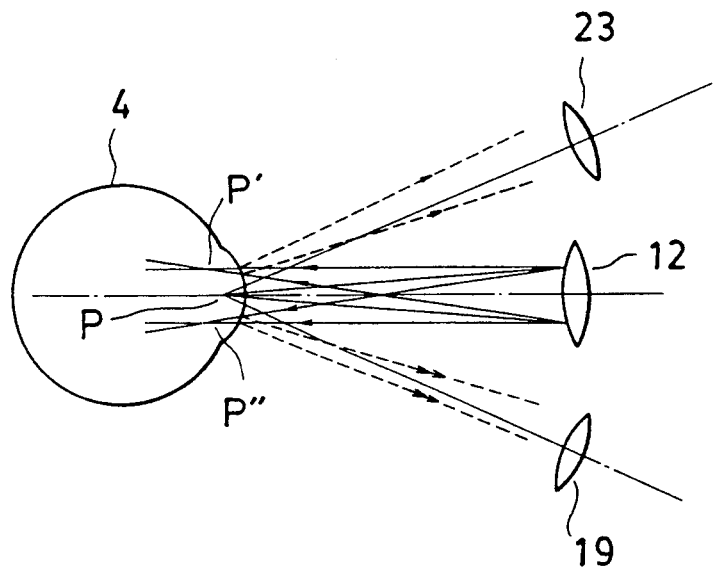
FIG. 3a is an explanatory drawing showing a plan view of the eye being scanned.
Figure 3B:
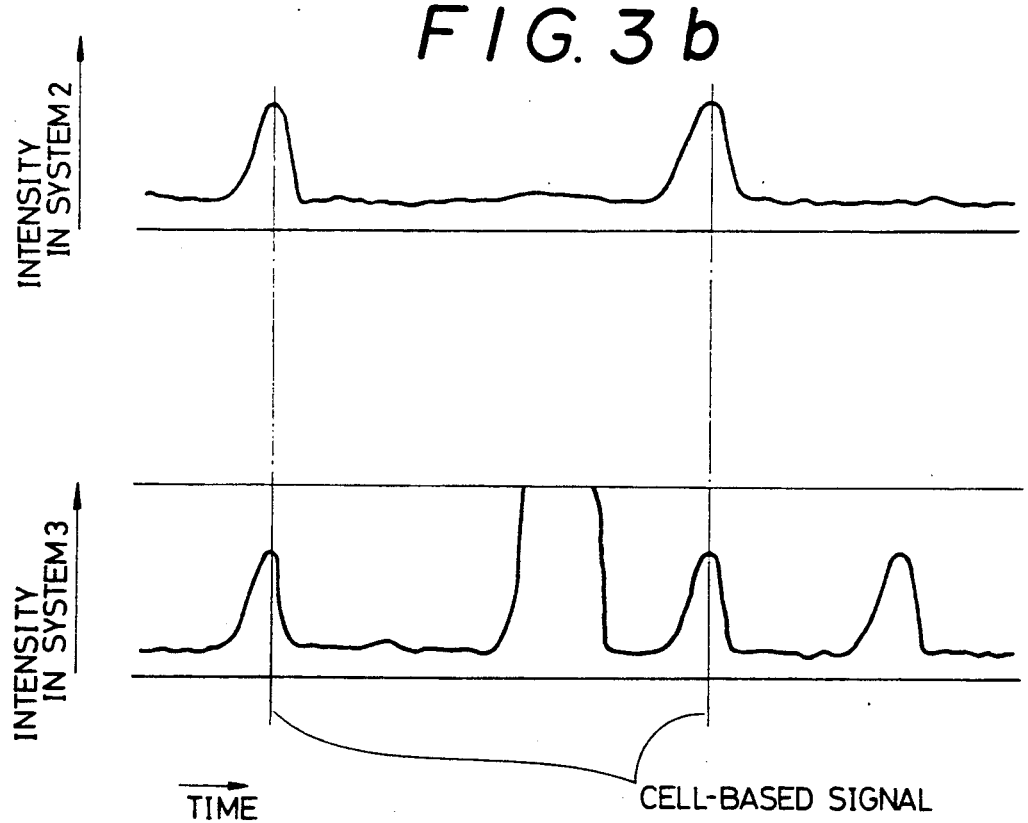

FIG. 3a shows a plan view of the scanning process. Using P' and P" to denote the ends of the horizontal raster, the course of the scanning is P→P'→P→P"→P. P, P' and P" are all arranged so that they come within the anterior chamber.

If the point of convergence is taken as being at P', light reflected by the cornea advances along the single-arrow broken line. This reflected light indicated by the single-arrow broken line has considerable directivity and luminance because P' is a point of convergence on which the laser beam is converged. At this time the reflected light passes through the lens 23 and impinges on the photoelectric converter 25. If the reflected light impinges directly, a signal will be produced that is far stronger than the signal from floating cells in the anterior chamber of the eye 4. On the other hand, if the reflected light is attenuated by the light-receiving optical system down to around the same strength as the light scattered by cells, it will become impossible to distinguish the reflected light signal from the signal produced by light scattered by cells. However, since the reflected light is strongly directional, it cannot enter the optical receiving system 2 because it is directed towards the optical receiving system 3. Similarly, when the point of convergence is at P'', reflected light indicated by the two-arrow broken line can enter the optical receiving system 2 but cannot at the same time enter the optical receiving system 3. The output signal of the optical receiving system 2 will thus differ from the output signal of the optical receiving system 3, as shown by FIG. 3b. Thus, cell-based scattered light signals can be discriminated from reflected light signals by regarding a signal as being a cell-based signal only when the light concerned enters both light-receiving systems simultaneously. This also applies to the discrimination of cell-based signals from signals originated by the light being reflected by a natural or artificial crystalline lens.

As shown in FIG. 3c, when cell-based signals in the output of the optical receiving system 2 are eclipsed by reflected light or other strong noise components, the harmful light rays can be counted as one pulse because the cell-based scattered light is received in the optical receiving system 2; when the direction in which the reflecting surface faces is not known, as in the case of an artificial crystalline lens or the like, that is, when the returning light is light reflected by the crystalline lens and has no connection with corneal reflected light, evaluation of the output of the light-receiving systems may be omitted to be on the safe side. While this will result in a lower count, it will not have a major impact.

Thus, optical information simultaneously input into the two light-receiving systems is detected as being information relating to the floating cells to be measured, while optical information input into just one light-receiving system is judged to be noise and is therefore not included in the measurement evaluation. This method provides an objective, quantitative measurement of floating cells in the anterior chamber of the patient's eye.

The effect of providing the masks 20 and 24 in front of the photoelectric converters 21 and 25 of the optical receiving system 2 will now be explained.

In general, an effective region is formed by providing an aperture-limiting mask in the vicinity of the image plane: this is termed the mask effect. Light produced outside the effective region is blocked by the mask.

In the example shown in FIG. 4b, a single mask (20, 24) is used for the lens (19, 23). In the figure, the effective region is indicated by the blacked-out portion. Light produced in this region can pass unhindered through the mask. The shaded portion is a partially effective region from which a certain proportion of light can pass through the mask. In the case of the present invention there are two light-receiving sections, which are provided with respective masks 20 and 24, thereby forming the effective region shown in FIG. 4a.

Here, FIG. 4c shows when $\alpha = \beta = 45°$. Noise components can be excluded if the effective region is formed only within the anterior chamber (that is, if the rays that give rise to noise do not come within the effective region), so that signals picked up simultaneously by each of the two light-receiving sections will be originated only from within the anterior chamber.

The measurement volume is determined by this effective region and the size of the raster scanning region R formed by the two-dimensional scanning shown in FIG. 5. If the raster is made larger than the effective region, the effective region itself becomes the measurement volume. A sufficiently large raster can be obtained by using a mydriatic, or dilated pupil so the measurement volume may be set by setting the size of the masks 20 and 24, i.e. of the effective region.

As long as the iris does not come within the effective region, the raster could be projected on the iris, even if a mydriatic is not used. However, because the intensity of light scattered by the iris is very high and increases the background noise, the laser beam should preferably not impinge on the iris. Thus, when measurements are being carried out without using a mydriatic, the size of the masks 20 and 24 and of the raster should be suitably decided in accordance with the requisite measurement volume, taking into account the above factors.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic measuring method in which an optical system is used to project a laser beam at a selected spot in a patient's eye, and the laser light scattered therefrom is detected for ophthalmic measurement, comprising the steps of:

projecting a laser beam at a selected spot at the camera oculi of an eye to be examined;

receiving light scattered therefrom in a first direction by means of a first photoelectric converter to produce a signal representing the intensity of the scattered light in the first direction;

simultaneously receiving light scattered in a second direction by means of a second photoelectric converter to produce a signal representing the intensity of the scattered light in the second direction, said first and second direction being arranged to the symmetrical with respect to the direction along which the laser beam is projected at the selected spot in the eye; and comparing the signals in the first and second directions to determine the presence of noise components derived from light reflected at a portion of the eye other than the selected spot in the eye and processing the signals to remove therefrom the noise components.

2. A method as set forth in claim 1, wherein the laser beam is deflected horizontally and vertically to scan the selected spot two-dimensionally.

3. A method as set forth in claim 1, wherein the noise signal is derived from the light reflected at the cornea or crystalline lens in the eye.

4. A method as set forth in claim 1, wherein the laser beam is projected at the selected spot in the eye from the front side of the eye to be examined.

5. An ophthalmic measuring apparatus in which an optical system is used to project a laser beams at a selected spot in a patient's eye, and the laser light scattered therefrom is detected for ophthalmic measurement, comprising:

a laser source for producing a laser beam;

means for projecting the laser beam at a selected spot in the camera oculi of the eye to be examined;

first light-receiving means arranged in a first direction with respect to the projecting means and provided with a first photoelectric converter for receiving light scattered from the selected spot in the camera oculi of the eye to produce a signal representing the intensity of the scattered light in the first direction;

second light-receiving means arranged in a second direction with respect to the projecting means and provided with a second photoelectric converter for simultaneously receiving light scattered from the selected spot in the camera oculi of the eye to produce a signal representing the intensity of the scattered light in the second direction;

said first and second light-receiving means being disposed symmetrically at each side of the laser beam projection means; and means for processing the signals obtained from the first and second light-receiving means to compare them to determine the presence of noise components derived from light reflected at a portion of the eye other than the selected spot in the eye and to remove the noise components.

6. An apparatus as set forth in claim 5, further comprising means for deflecting the laser beam horizontally and vertically to scan the spot to be measured two-dimensionally.

7. An apparatus as set forth in claim 5, further comprising an optical observation system for observing the state of the laser beam projection.

8. An apparatus as set forth in claim 5, wherein the laser beam projection means are disposed in the vicinity of the front of the eye to be examined.

9. An apparatus as set forth in claim 7, wherein the optical observation system is disposed in the vicinity of the front of the eye to be examined.

10. An apparatus as set forth in claim 9, wherein the laser light projection means and at least the portion of the optical observation system are integrated.

11. An apparatus as set forth in claim 5, wherein an optical mask is disposed in front of the photoelectric converter in the first and second light-receiving means, respectively, to define a measurement region corresponding to the shape of the optical mask.

* * * * *